(12) United States Patent
Ferko

(10) Patent No.: US 11,491,016 B2
(45) Date of Patent: Nov. 8, 2022

(54) PATIENT SPECIFIC BONE PREPARATION FOR CONSISTENT EFFECTIVE FIXATION FEATURE ENGAGEMENT

(71) Applicant: Stryker Corporation, Kalamazoo, MI (US)

(72) Inventor: Michael C. Ferko, Warwick, NY (US)

(73) Assignee: Stryker Corporation, Kalamazoo, MI (US)

(*) Notice: Subject to any disclaimer, the term of this patent is extended or adjusted under 35 U.S.C. 154(b) by 1133 days.

(21) Appl. No.: 16/053,957

(22) Filed: Aug. 3, 2018

(65) Prior Publication Data

US 2018/0338839 A1 Nov. 29, 2018

Related U.S. Application Data

(63) Continuation of application No. 14/489,884, filed on Sep. 18, 2014, now Pat. No. 10,166,109.

(Continued)

(51) Int. Cl.
*A61F 2/38* (2006.01)
*A61B 5/00* (2006.01)
(Continued)

(52) U.S. Cl.
CPC .............. *A61F 2/38* (2013.01); *A61B 5/0073* (2013.01); *A61B 5/4509* (2013.01);
(Continued)

(58) Field of Classification Search
CPC combination set(s) only.
See application file for complete search history.

(56) References Cited

U.S. PATENT DOCUMENTS 5,172,695 A 12/1992 Cann et al.
5,925,049 A * 7/1999 Gustilo ............... A61B 17/155
606/88

(Continued)

FOREIGN PATENT DOCUMENTS

CN 101106189 A 1/2008
KR 20120092451 A 8/2012
(Continued)

OTHER PUBLICATIONS

Carter, Dennis R., "The compressive behavior of bone as a Two-Phase Porous Structure", The Journal of Bone and Joint Surgery, vol. 59-A, No. 7, Oct. 1977, pp. 954-962.
(Continued)

*Primary Examiner* — Javier G Blanco
(74) *Attorney, Agent, or Firm* — Lerner, David, Littenberg, Krumholz & Mentlik, LLP

(57) ABSTRACT

An optimized press-fit between a resected bone and an articular implant may, for instance, reduce undesirable qualities, including excess micromotion, stress transmission, and/or strain. By taking into account heterogeneous bone properties, the parameters of a bone resection can be determined as to optimize the press-fit between a resected bone and an articular implant. An optimized press-fit is obtained by determining ideal engagement characteristics corresponding to the fit between the fixation features of an articular implant and a bone. Then, taking into account a bone's heterogeneous properties, the parameters of a bone resection that would substantially achieve the determined ideal engagement characteristics are determined.

6 Claims, 9 Drawing Sheets

Related U.S. Application Data

(60) Provisional application No. 61/879,360, filed on Sep. 18, 2013.

(51) Int. Cl.

| | | |
|---|---|---|
| *A61B 17/17* | (2006.01) | |
| *A61F 2/30* | (2006.01) | |
| *A61F 2/28* | (2006.01) | |
| *A61B 6/03* | (2006.01) | |
| *G06F 30/20* | (2020.01) | |
| *A61B 6/00* | (2006.01) | |
| *G16H 50/50* | (2018.01) | |
| *A61B 17/15* | (2006.01) | |

(52) U.S. Cl.
CPC ............ *A61B 5/4528* (2013.01); *A61B 6/032* (2013.01); *A61B 17/17* (2013.01); *A61F 2/28* (2013.01); *A61F 2/30942* (2013.01); *G06F 30/20* (2020.01); *A61B 6/505* (2013.01); *A61B 17/155* (2013.01); *A61F 2/389* (2013.01); *A61F 2/3859* (2013.01); *A61F 2002/30006* (2013.01); *A61F 2002/30014* (2013.01); *A61F 2002/30943* (2013.01); *A61F 2002/30948* (2013.01); *G16H 50/50* (2018.01)

(56) References Cited

U.S. PATENT DOCUMENTS

| | | | |
|---|---|---|---|
| 7,584,080 B2 | 9/2009 | Taylor et al. | |
| 7,618,451 B2 | 11/2009 | Berez et al. | |
| 7,995,822 B2 | 8/2011 | Lang et al. | |
| 8,126,234 B1 | 2/2012 | Edwards et al. | |
| 8,457,930 B2 | 6/2013 | Schroeder | |
| 8,644,568 B1 | 2/2014 | Hoffmann et al. | |
| 8,781,191 B2 | 7/2014 | Lang et al. | |
| 8,855,389 B1 | 10/2014 | Hoffmann et al. | |
| 9,743,940 B2 | 8/2017 | Catanzarite et al. | |
| 9,931,218 B2 | 4/2018 | May et al. | |
| 2007/0100462 A1 | 5/2007 | Lang et al. | |
| 2008/0234833 A1 | 9/2008 | Bandoh et al. | |
| 2009/0204226 A1 | 8/2009 | Fonte | |
| 2011/0087332 A1* | 4/2011 | Bojarski ............ | A61B 17/1764 623/20.32 |
| 2011/0087465 A1 | 4/2011 | Mahfouz | |
| 2012/0265496 A1 | 10/2012 | Mahfouz | |
| 2012/0323244 A1* | 12/2012 | Cheal ................... | A61B 34/10 606/130 |
| 2012/0323246 A1 | 12/2012 | Catanzarite et al. | |
| 2012/0330429 A1 | 12/2012 | Axelson, Jr. et al. | |
| 2013/0211531 A1 | 8/2013 | Steines et al. | |
| 2014/0121715 A1 | 5/2014 | May et al. | |
| 2014/0257293 A1 | 9/2014 | Axelson, Jr. et al. | |
| 2015/0119987 A1 | 4/2015 | Davignon et al. | |
| 2015/0265292 A1 | 9/2015 | Olson | |
| 2017/0035513 A1 | 2/2017 | Mahfouz et al. | |
| 2017/0164962 A1 | 6/2017 | Olson | |
| 2017/0325828 A1 | 11/2017 | Catanzarite et al. | |

FOREIGN PATENT DOCUMENTS

| | | |
|---|---|---|
| WO | 2008021494 A2 | 2/2008 |
| WO | 2013170872 A1 | 11/2013 |

OTHER PUBLICATIONS

Donnelly, "Methods for Assessing Bone Quality," Published online: Nov. 30, 2010, © The Association of Bone and Joint Surgeons® 2010.

Gargiulo, Paolo; Petursson, Throstur; Magnusson, Benedikt; Bifulco, Paolo; Magnusdottir, GiGJA; Halldorsson, Gretar et al.: "Assessment of Total Hip Arthroplasty by Means of Computed Tomography 3D Models and Fracture Risk Evaluation" Artificial Organs, vol. 37, No. 6, Jun. 1, 2013 (Jun. 1, 2013), XP002732374, DOI: 10 .1111jaor. 12033 p. 567-p. 573.

Gopalakrishman et al., "Magnitude of Cement-Device Interfacial Stresses with and without Tibial Stemming: Impact of BMI", The Journal of Knee Surgery, vol. 24, No. 1, 2011.

Haddad et al., "Fracture prediction of cardiac lead medical devices using bayesian networks", Proceedings of the ASME 2013 Conference on Frontiers in Medical Devices: Application of Computer Modeling and Simulation, FMD2013, Sep. 11-13, 2013, Washington, DC, USA.

International Search Report and Written Opinion for Application No. PCT/US2014/056261 dated Dec. 18, 2014.

International Search Report and Written Opinion for Application No. PCT/US2014/062565 dated Jan. 22, 2015.

Kaneko et al., Mechanical properties, density and quantitative CT scan data of trabecular bone with and without metastases, Journal of Biomechanics 37, (2004) 523-530.

Klever, F.J. et al., Global mechanical properties of trabecular bone: experimental determination and prediction from structural model. Biomechanics: Current [4]Interdisciplinary Research: The Netherlands, 1985, 167-72.

Rho, et al., "Relations of mechanical properties to density and CT numbers in human bone," Med. Eng. Phys. vol. 17, No. 5, pp. 347-355, 1995.

Scola et al., "Mechanical quantification of local bone quality in the humeral head: A feasibility stody", The Open Orthodaedics Journal, 2013, 7, 172-176.

\* cited by examiner

PATIENT SPECIFIC BONE PREPARATION FOR CONSISTENT EFFECTIVE FIXATION FEATURE ENGAGEMENT

CROSS-REFERENCE TO RELATED APPLICATIONS

The present application is a continuation of U.S. patent application Ser. No. 14/489,884, filed Sep. 18, 2014, which claims the benefit of the filing date of U.S. Provisional Patent Application No. 61/879,360 filed Sep. 18, 2013, the disclosures of which are both hereby incorporated by reference herein.

FIELD OF THE INVENTION

The present invention relates to systems and methods for optimizing surgical plans and in particular relates to the use of image data obtained from patients to determine optimal properties for effective implant engagement.

BACKGROUND OF THE INVENTION

In cementless orthopedic procedures robust biologic ingrowth may be a key element to long-term implant stability and performance. Biologic ingrowth may require sufficient stability of the implant with respect to adjacent bones and/or tissues, particularly during the first 6-8 months after implantation. During this time, bone growth onto a roughened surface or into a porous surface may only occur if the implant is held stable with respect to the bone. Ideally, in order to achieve desired stability, motion of the implant relative to the bone should be less than 150 microns particularly in the liftoff (i.e. normal) and sheer (i.e. bi-directional) directions with respect to the plane of the porous or roughened surface.

Implant manufacturers routinely utilize a variety of design features to attempt to provide a press-fit that aids in limiting the movement of the implant relative to surrounding anatomical structures. Fixation features such as pegs and keels, for example, generally include designed surface textures to increase the coefficient of friction between the implant and the surrounding anatomical structures. These implant fixation features may result in increasing success of cementless implants. However, bone quality including bone density, porosity, and elastic modulus, for example, varies from patient to patient and also varies by location within a particular patient. Variability in bone quality at the location which bone contacts fixation features results in variable effect of fixation and subsequently may result in deviations of the implant stability from the design intent.

BRIEF SUMMARY OF THE INVENTION

A first aspect of the present disclosure is to take advantage of information derived about bone quality in order to optimize bone preparation and to obtain a consistent press-fit of implant fixation features from patient to patient in accordance with the design intent of the implant. Bone quality information can be determined from a variety of methods preoperatively and/or intraoperatively. Once information about bone quality is obtained, preparation for implant fixation features can be modified such that there is increasing interference between the implant and adjacent bone for decreasing bone quality, and decreasing interference between the implant and adjacent bone with increasing bone quality.

With recent attention being paid to preoperative planning such as in the design and manufacture of custom implants and in determining the position and movement of robotic arms, for example, there is also a great opportunity to leverage these techniques with information about bone quality obtained in preoperatively obtained scans of the anatomy of the patient. Bone quality information can be ascertained or estimated from preoperative images obtained via computed tomography ("CT"), magnetic resonance imaging ("MRI"), and x-ray imaging, for example. Within the resolution of the preoperative scan, bone quality information can be obtained and subsequently mapped onto the location where a fixation feature will be implanted based on an operative plan. Based on the implant design intent, a specific volume of bone may be removed from the preoperatively planned implanted location of the fixation feature, with the remaining bone to serve as in an initial interference or press-fit relationship with the implant. The implant will preferably be designed to provide a specific initial stability which will be a function of the bone properties the fixation feature was designed to engage and the volume of bone to be displaced during bone removal. Preferably, the volume of the amount of bone removed is less than the volume of the fixation feature implanted into the bone such that initial interference is created. The volume of bone removed may therefore be referred to as under-preparation.

One embodiment of the first aspect of the present disclosure includes a method of determining one or more parameters of a bone resection for receiving a fixation feature of an implant. The method includes the steps of obtaining bone quality data corresponding to a bone of a joint. One or more desired engagement characteristics corresponding to a desired press-fit between the fixation feature and the bone may be determined. The one or more parameters of the bone resection may be determined based on the bone quality data in order to substantially achieve the one or more desired engagement characteristics between the bone and the fixation feature.

The bone quality data may be derived from image data, which may be CT image data. The step of obtaining bone quality data may include calculating one or more Hounsfield values from the CT image data. The bone quality data may be derived from image data of a single individual, or data corresponding to a population. The one or more desired engagement characteristics may include a desired bone displacement by the fixation feature or a desired static frictional force acting on the fixation feature. The bone quality data may be bone density or elastic modulus. The fixation feature may be a peg, and the parameters of the bone resection may correspond to peg depth or peg radius. The fixation feature may be a keel. The parameters may alternately correspond to the distance between at least two substantially opposing prepared bone surfaces, and the fixation feature may include substantially opposing implant surfaces. The above described steps may be performed intraoperatively. A computer program may comprise instructions which, when executed on at least one processor, causes the at least one processor to carry out the method according to any one or more of the steps described above.

Although CT image data is described, the image data may include MRI image data, x-ray image data, or any other image data obtained by a suitable imaging method known in the art, including but not limited to ultrasound image data, nuclear imagining image data, radioisotope image data, or electrical impedance tomography image data. In still yet another embodiment, the image data may comprise a combination of one or more different kinds of image data.

According to another aspect of the disclosure, a method of determining one or more parameters of a patient-specific surgical tool for preparing a bone to receive a fixation feature of an implant includes obtaining bone quality data corresponding to the bone. One or more desired engagement characteristics corresponding to a desired press-fit between the fixation feature and the bone may be determined. The one or more parameters of the patient-specific surgical tool may be determined based on the bone quality data in order to substantially achieve the one or more desired engagement characteristics between the bone and the fixation feature. The patient-specific surgical tool may be a tool for drilling or cutting, or a guide for drilling or cutting. The one or more desired engagement characteristics may include a desired bone displacement by the fixation feature or a desired static frictional force acting on the fixation feature. A computer program may comprise instructions which, when executed on at least one processor, causes the at least one processor to carry out the method according to any one or more of the steps described above.

According to yet another aspect of the disclosure, a system for determining one or more parameters relating to bone quality of at least one joint includes a device and a computer. The device may be for obtaining bone quality data corresponding to a bone of the joint. The computer may be adapted to determine the one or more parameters based on the bone quality data in order to substantially achieve one or more desired engagement characteristics between the bone and a fixation feature of the implant. The one or more desired engagement characteristics may correspond to a desired press-fit between the fixation feature and the bone. The device may include a CT scanning device, and the bone quality data may be derived from CT images, for example by using one or more Hounsfield values. The one or more desired engagement characteristics may include a desired bone displacement by the fixation feature or a desired static frictional force acting on the fixation feature. The bone quality data may be bone density or elastic modulus. The fixation feature may be a peg. At least one of the parameters may correspond to peg radius and/or peg depth. The fixation feature may alternately be a keel. The device may be configured to obtain bone quality data intraoperatively.

According to still a further embodiment of the disclosure, a system for determining one or more parameters of a patient-specific surgical tool includes a device and a computer. The device may be configured to obtain bone quality data corresponding to a bone of a joint. The computer may be adapted to determine the one or more parameters of the patient-specific surgical tool based on the bone quality data in order to substantially achieve one or more desired engagement characteristics between the bone and a fixation feature of an implant. The desired engagement characteristics may correspond to a desired press-fit between the fixation feature and the bone. The patient-specific surgical tool may be a drilling or cutting tool, or a guide for drilling or cutting. The one or more desired engagement characteristics may include a desired bone displacement by the fixation feature or a desired static frictional force acting on the fixation feature.

BRIEF DESCRIPTION OF THE DRAWINGS

The present disclosure will be better understood on reading the following detailed description of embodiments thereof, and on examining the accompanying drawings, in which.

DETAILED DESCRIPTION

By taking into account heterogeneous bone properties, the parameters of a bone resection can be determined as to optimize the press-fit between a resected bone and an implant, such as an articular implant. An optimized press-fit between a resected bone and an articular implant may, for instance, reduce undesirable qualities, including excess micromotion, or maintain a desirable range for other qualities, including stress transmission and strain. The optimized press-fit is obtained by determining ideal engagement characteristics of fixation features of the articular implants and then determining the parameters of a bone resection that would substantially achieve the determined ideal engagement characteristics.

Figure 1:
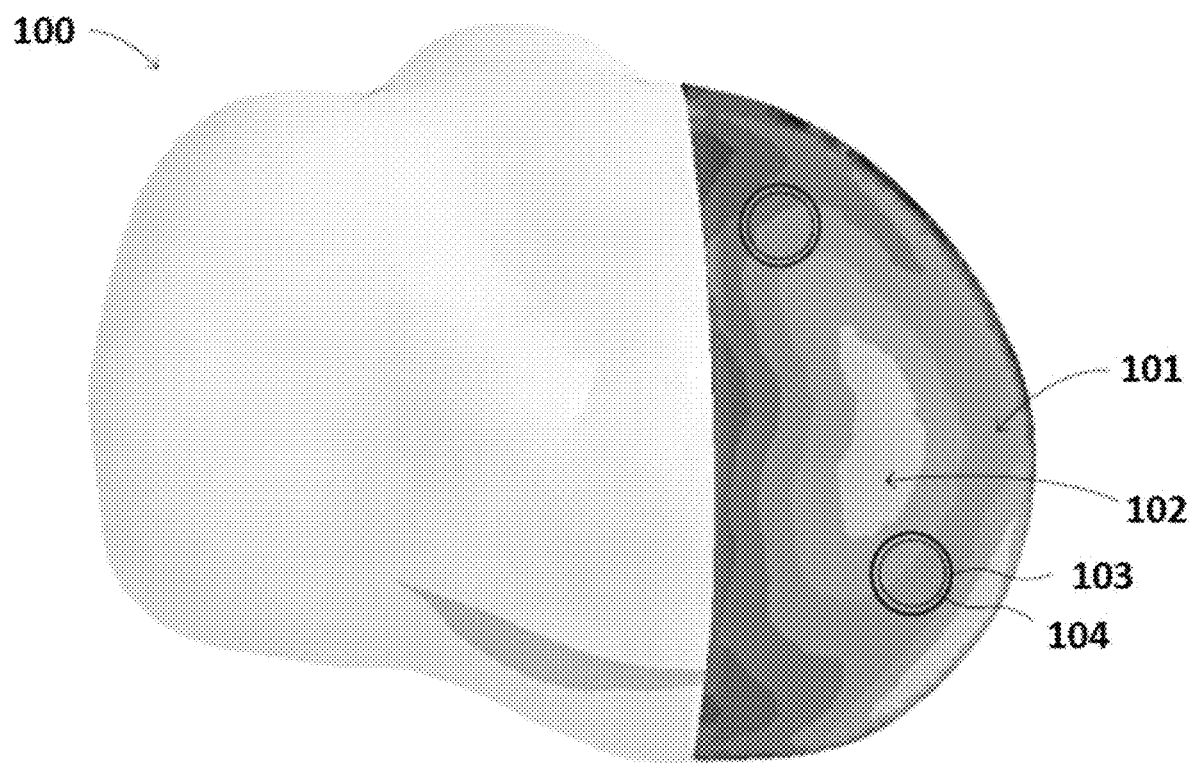
FIG. 1 is an example of an average bone density profile with a corresponding designed implant preparation.

In FIG. 1, one example of an average bone density profile is presented. The bone density profile 100 exhibits areas of both relatively low density 101 (indicated by relatively dark shading) and relatively high density 102 (indicated by relatively light shading). FIG. 1 also exhibits an example of a planned parameter 104 of a bone resection in order to achieve a press fit with a fixation feature having a certain preoperatively planned shape. Outline 103 represents the size of the fixation feature of the implant. Here, planned parameter 104 is shown as a circular cross-section of a hole to be formed in the bone. This cross-section may be made with a rotating burr plunged into the bone a certain preoperatively planned depth. In another embodiment, planned parameter 104 may have more of an ovular cross-section as viewed in the same plane if a rotating burr, for instance, is plunged into the bone at a certain preoperatively planned angle. Although the fixation feature is shown with circular outline 103, the fixation feature may have an irregular shape in other embodiments in which its cross-sectional shape is designed based on preferred clearances and tolerances with planned parameter 104. Of course, planned parameter 104 may have an irregular shape in other embodiments in which its cross-section shape is designed based on preferred clearances and tolerance with fixation feature 103. Planned parameter 104 may include bone preparation with designed areas having accurate tolerance profiles to enable improved initial fixation and stability for cementless implants and to improve long-term bone ingrowth/ongrowth to an implant. Systems and methods of bone preparation with specifically designed regions having increased levels of accuracy are shown and described in U.S. Pat. Pub. No. 2014/0257293 ("the '293 Publication") titled "Bone Pads," the disclosure of which is hereby incorporated by reference herein. Further, the '293 Publication discloses methods of implanting prostheses onto these accurate tolerance profiles. Examples of preferred clearances and tolerances with respect to fixation features 103 having curved keels, for example, are discussed in greater detail below.

Figure 2:
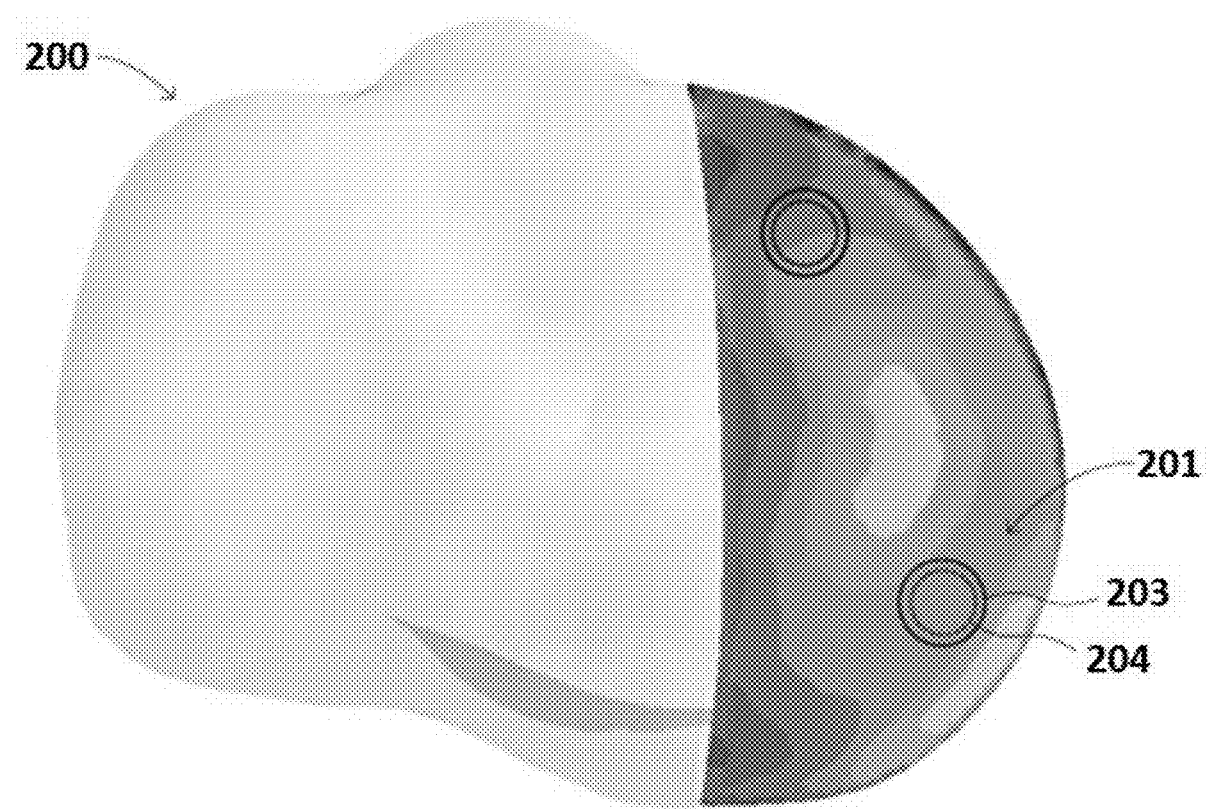
FIG. 2 is an example of a bone density profile exhibiting decreased density, and a corresponding implant preparation.

FIG. 2 illustrates one example of a bone density profile exhibiting decreased bone density compared to that shown in FIG. 1. The bone density profile 200 exhibits increased areas of lower density bone 201 in planned fixation feature implant positions than in bone 101 shown in FIG. 1. In order to achieve the designed press-fit between the fixation feature and the lower density bone, the parameter of the resection 204 is adjusted with respect to the shape of the fixation feature shown as outline 203. Here, resection 204 is modified to a lesser diameter compared to resection 104, thus increasing the interference between the fixation feature of the implant and the bone.

Figure 3:
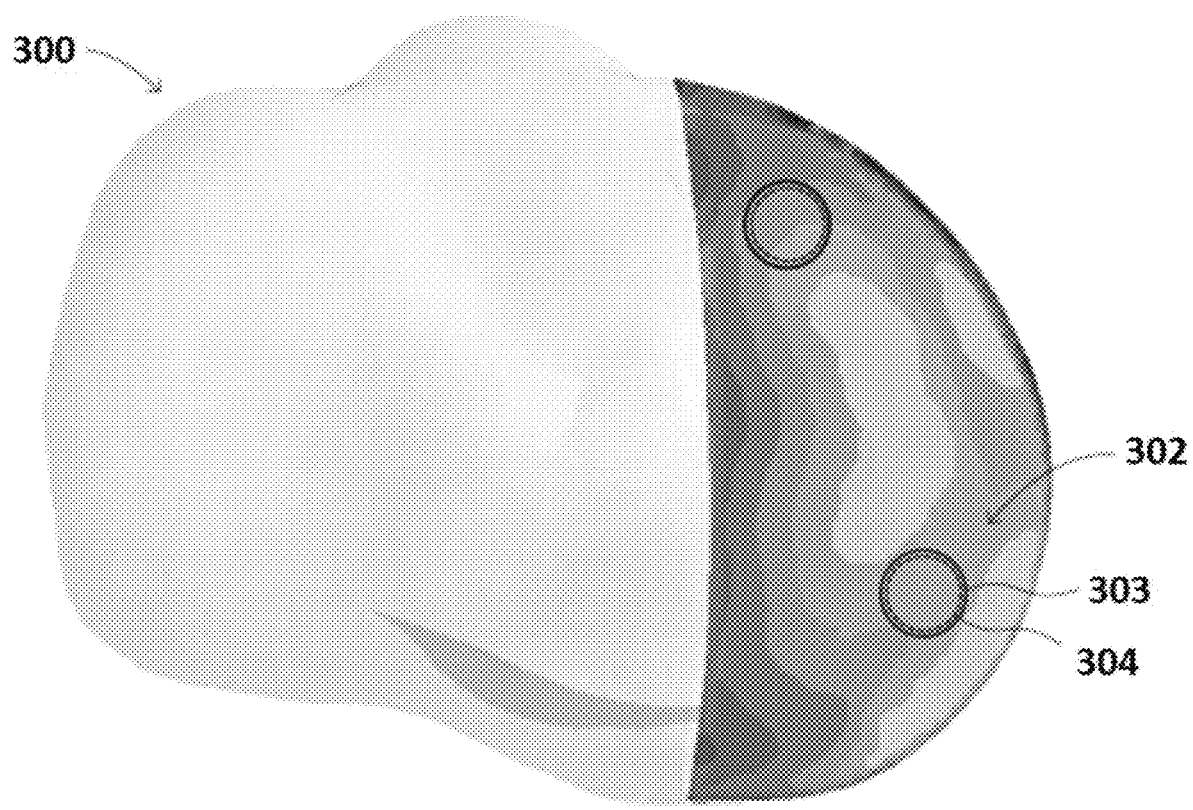
FIG. 3 is an example of a bone density profile exhibiting increased density, and a corresponding implant preparation.

FIG. 3 illustrates one example of a bone density profile exhibiting increased bone density compared to that shown in FIG. 1. The bone density profile 300 exhibits increased areas of higher density bone 302 in planned fixation feature implant positions than in bone 101 shown in FIG. 1. In order to achieve the designed press-fit between the fixation feature and the bone, the parameters of the resection 304 are adjusted with respect to the shape of the fixation feature shown as outline 303. Here, resection 304 is modified to a larger diameter, thus decreasing the interference between the fixation feature and the bone.

Bone quality data may be derived from an image (or data relating to an image) of at least one joint. The image (or image data) can be obtained in a variety of ways, including by performing any medical imaging method known in the art, or by obtaining the image data from a collection and/or database. For example, the image data may be obtained by performing a CT scan. Additional suitable imaging methods include MRI, Electrical Impedance Tomography ("EIT"), Dual-Energy X-ray Absorptiometry ("DXA" or "DEXA"), X-ray, ultrasound, and nuclear imaging, for example. The image data may further comprise a combination of one or more different kinds of image data, for instance a composite image data that comprises both CT and MRI image data, for example.

The image data obtained may correspond to either a single individual or to a population of individuals. For instance, the image data may correspond to a joint of the individual for whom the press-fit is being optimized in accordance with the method(s) described herein. In this case, the parameters of the bone resection are being determined on a patient-specific basis such that the parameters optimize the press-fit between the individual anatomy and the articular implant. On the other hand, bone quality may be derived from data representative of a population, for instance a representative or average data corresponding to a particular population of individuals. The population may represent a class or subclass of individuals, for instance members of an age-range, a gender, a class of individuals who suffer from a particular joint or knee ailment, any other suitable population that is relevant to articular implants, or any combination thereof. For example, the Stryker Orthopaedics Modeling and Analytics system ("SOMA") is a population-based design environment featuring a large database of bone morphology, including size, shape, density, and inner and outer cortical boundaries, drawn from diverse populations. Such a database may be used for example by normalizing a set of data relevant to the patient of interest onto a phantom tissue model. In this way, image data taken from a population may be used to derive the relevant bone quality and to optimize the engagement between the implant and the patient's bone.

Once the image data of at least one joint is obtained, bone quality information can be derived by a variety of methods for calculating or estimating bone properties from the imaging modalities previously described, including CT, X-ray, MRI, DEXA, etc.

By way of example, bone density and elastic modulus can be derived from a CT image (or data relating to the image) by correlating CT brightness to bone density and then to elastic modulus using Hounsfield values (also known as CT numbers). Bone density of both the proximal end of the tibia and the distal end of the femur can be calculated from CT brightness values by the following equations:

A) Proximal Tibia:
Hounsfield unit to density conversion:

$$\rho=1.14e^{-4}+(9.16e^{-7})*(CT\#), \text{ where } \rho \text{ is in g/mm}^3$$

B) Distal Femur:
Hounsfield unit to density conversion:

$$\rho=1.39e^{-4}+(1.205e^{-6}*)*(CT\#), \text{ where } \rho \text{ is in g/mm}^3$$

Further, the elastic modulus of both the proximal end of the tibia and the distal end of the femur can be calculated from the derived density values by the following equations:

A) Proximal Tibia:
Density to modulus conversion:

$$E=(1.2965e^8)*(\rho^{1.5}), 0<\rho\leq0.001 \text{ g/mm}^3$$

$$E=(3.790e^{12})*(\rho^3), 0.001<\rho\leq0.00173 \text{ g/mm}^3$$

B) Distal Femur:
Density to modulus conversion:

$$E=(1.283e^9)*(\rho^{1.85}), 0<\rho\leq0.001 \text{ g/mm}^3$$

$$E=(3.790e^{12})*(\rho^3), 0.001<\rho\leq0.00173 \text{ g/mm}^3$$

The aforementioned examples are only examples of how to derive bone property information from the image data of at least one joint. Similar methods exist and are known in the art related to other forms of image data and other bone properties.

An articular implant may have any number of fixation features for attaching the implant to the bone during implantation. For example, one fixation feature may be a peg extending from the bone-contacting surface of the articular implant. The peg may then be received by the bone during implantation of the implant and may act as to fix the position of the articular implant relative to the bone. Fixation fixture such as pegs and keels are shown and described in U.S. Pat. Pub. No. 2012/0330429 ("the '429 Publication") titled "Prosthetic Implant and Method of Implantation," the disclosure of which is hereby incorporated by reference herein. The fixation features may protrude outwardly from the bone-contacting surface in normal and/or angled directions. Further, as described in the '429 Publication, the pegs and keels may have a curved shape. The bone contacting geometry of the articular implant may also constitute a fixation feature. For instance, the surface of the implant that contacts the bone during implantation may be designed as to promote adherence between the implant and the bone. These fixation features are presented by way of example only, and an implant may include any one or a combination of these fixation features, and may also be used in conjunction with any other suitable fixation feature known in the art.

Ideal engagement characteristics are determined that would represent an ideal press-fit between an implant and bone. The characteristics that represent an ideal press-fit are preferably then held constant across implantation procedures, taking into account bone properties such as density.

For instance, it could be determined that a specific mass of the bone displaced by a fixation feature represents an ideal engagement. Therefore, the amount of displaced mass may be identified as an ideal engagement characteristic. In another example, it could be determined that a particular frictional force along a fixation feature represents an ideal engagement. In that case, that frictional force along the fixation feature may be identified as an ideal engagement characteristic. There are numerous options for what factors to hold constant to represent an ideal implant/bone engagement, or effective press-fit, from patient to patient. It should be understood that the term "ideal engagement characteristic" need not refer to an actually perfect engagement characteristic, but is rather used to refer to a desired engagement characteristic. Similarly, the term "optimal" is used herein, for example regarding an optimal press-fit. It should be understood that the term modified by "optimal" need not mean perfect, but rather is used to refer to a desired characteristic.

Determining the parameters for achieving an ideal engagement characteristic may include designing the bone resection to receive peg depth, peg radius, and/or bone contacting geometry of a fixation feature of the corresponding implant. Therefore, the parameters may include the radius of a bore hole, the depth of a bore hole, the shape of the bore hole, and/or the shape of the implant receiving surface, for example. However, the precise method of determining the parameters of the resection depends on the nature of the ideal engagement characteristics. For example, the engagement characteristic need not be an interference fit between a peg and a hole. During a knee arthroplasty procedure, the desired engagement characteristic may be the geometrical fit between the resected bone and the implant. This may be achieved by altering the path of a robotic milling tool based on bone quality information obtained from image data. The concepts disclosed herein may also be applied to a variety of other implants or implant systems, as described in greater detail below.

A. Density—Mass Displacement

Where the ideal engagement characteristic is the displacement of a determined mass of bone by a fixation feature, simple geometry may be utilized to adapt the parameters of the resection to heterogeneous bone properties, where:

$$M_{design} = M_{plan}$$

or $$\rho_{design} * V_{design} = \rho_{plan} * V_{plan}$$

Here, V refers to a volume of bone displaced, ρ refers to a bone density, "design" designates the fit or value that was intended or designed without taking into account heterogeneous bone properties, and "plan" represents the adjusted parameter taking into account heterogeneous bone properties.

For example, if using a simple cylindrical peg, the planned radius of preparation can be solved by substituting the formula for volume of a hollow cylinder $\pi L(R_{peg}^2 - R_{prep}^2)$:

$$\rho_{design} * \pi L(R_{peg}^2 - R_{prep-design}^2) = \rho_{plan} * \pi L(R_{peg}^2 - R_{prep-plan}^2)$$

or $$R_{prep-plan} = \sqrt{\{[(\rho_{design} * R_{prep-design}^2) + (\rho_{plan} * R_{peg}^2) - (\rho_{design} * R_{peg}^2)]/\rho_{plan}\}}$$

Here, $R_{prep-design}$ refers to the designed bone preparation radius, $R_{prep-plan}$ refers to the derived patient-specific bone preparation radius, and L refers to the peg length. In the example of a cylindrical peg 5 mm in diameter (2.5 mm radius) were designed to have 1 mm of diametric interference (0.5 mm radial interference) over a 10 mm length, the volume of bone displaced by design would be:

$$(\pi)(2.5 \text{ mm})^2(10 \text{ mm}) - (\pi)(2.5 \text{ mm} - 0.5 \text{ mm})^2(10 \text{ mm}) = 70.65 \text{ mm}^3.$$

If the peg were designed to optimally engage with 1.5 mg/mm³ cancellous bone, the mass of bone displaced would be approximately 105.98 mg by design. If the average density of bone surrounding the peg were calculated to be 1.25 mg/mm³ from preoperative image data, then the required patient-specific radial press-fit for the plan to gain equivalent mass displacement would be:

$$R_{prep-plan} = \sqrt{\{[(1.5 * 2^2) + (1.25 * 2.5^2) - (1.5 * 2.5^2)]/1.25\}} = 1.88 \text{ mm}$$

B. Elastic Modulus—Friction Force

It may be determined that the ideal engagement characteristic is the frictional force exerted on a fixation feature by the bone. In order to determine the extent to which resection parameters are modified as a function of patient specific modulus, a variety of methods may be used for obtaining extraction force for a particular implant design. For example, physical tests with bone analogs, cadaveric bones, or animal specimens can be used to directly measure extraction forces as a function of varying bone quality. Alternatively, computational models (e.g. finite element analysis) may be used to empirically solve for bone resection parameters as a function of varying density. Also, simplified geometry may be employed with hand calculations to adapt the parameters of the bone resection to include the known heterogeneous bone properties. The formula for static friction force between two objects is defined by:

$$F = \mu A P$$

where μ is the coefficient of static friction, A is the area of contact, and P is the contact pressure between the objects.

For example, in the case of a simple cylindrical implant peg where we assume the implant stiffness is much greater than the bone (i.e. the implant is non-deformable) and where the preparation (peg prep diameter) is much smaller than the surrounding bone, the bone can be simply viewed as a thick walled hollow cylinder. Therefore:

$$F = 2\pi r_{prep} L_{peg} \mu P$$

Since the peg is assumed not to deform, the pressure on the surface of the peg is driven by the deformation of the bone from the interference. If the bone is assumed to be elastic over the range of possible deformation, then the pressure is driven by the elastic deformation and results from tangential and radial stresses. Therefore:

$$\Delta r_{bone} = [r_{prep}/E_{bone}] * [\sigma\theta - \gamma_{bone} * \sigma r]$$

where σθ is the tangential stress, $\gamma_{bone}$ is the Poisson's ratio of the bone, and σr is the radial stress. Further, $$\Delta r_{bone} = [r_{prep} * P/E_{bone}] * [1 + \gamma_{bone}]$$

$$P = [(\Delta r_{bone} * E_{bone})/r_{prep} * (1 - \gamma_{bone})]$$

$$F = 2\pi r_{prep} L_{peg} * [(\Delta r_{bone} * E_{bone})/r_{prep} * (1 - \gamma_{bone})]$$

So for constant frictional force (per design intent), the interference can be calculated from:

$$\Delta r_{bone} = [F * (1 - \gamma_{bone})]/[\pi \mu L_{peg} E_{bone}]$$

In this case elastic modulus may be calculated by first finding the density of the bone based on CT brightness value via the above formulae, then applying the appropriate formula for E based on the density value. Holding the frictional force constant, the interference can be calculated for bone with varying elastic modulus.

Other calculations and sets of assumptions can be made to obtain an empirical formula for the appropriate interference amount needed to obtain a consistent and effective press-fit from patient to patient. Empirical testing (cadaveric, bone analog, or others) may also be done to obtain experimental values for the same.

Alternatively, an implant design may have utilized a framework for determining optimal fixation feature placement for a population based on bone quality information, as described in greater detail in U.S. Provisional Patent Application No. 61/896,335, filed Oct. 28, 2013 by named inventors Robert Davignon and Michael C Ferko. Consequently, a finite element analysis model may have been developed to calculate the response of a parameter of interest such as implant micromotion relative to design input parameters such as peg location. Utilizing the same finite element model, an implant designer could then supply another parameter or parameter input, for example fixation feature interference and/or bone quality information underlying the implant and/or surrounding the fixation feature. This adapted model could then test the response of the parameter of interest relative to varying regional and/or whole bone properties. In that way, a second response equation could be developed to directly supply information about required relative fixation feature interference relative to bone quality.

As noted above, although a number of examples are given in which a fixation feature takes the form of a straight cylindrical peg, this is for purposes of illustration only. The examples above may be applied to (with or without modification, as necessary) to other types of fixation features, such as the curved keels described in the '429 Publication.

Rather than determining heterogeneous bone properties preoperatively, there is also an option of testing for bone quality intraoperatively, at the time of surgery, and then adjusting the resection parameters in real-time. This embodiment obviates the need for preoperative image data. For instance, image data may be collected intraoperatively, and a robotic constraint model or a robotic milling path can be utilized to make bone preparations. Such bone preparations utilizing robotics are disclosed in U.S. Ser. No. 61/775, 045 titled "Bone Pads," the disclosure of which is hereby incorporated by reference herein.

For example, during an implant procedure, a surgeon may use a mechanical tool to determine the density of the bone at the site(s) at which the fixation features of the implant are intended to be inserted. Assume the implant includes a fixation feature in the form of a straight cylindrical peg with a diameter of 5 mm (2.5 mm radius) designed to have a diametric interference of 1 mm (0.5 radial interference). Also assume that the surgeon determines with the mechanical tool that the patient's bone density at the site of interest is less than the design plan of the implant. The surgeon could quickly calculate a modified interference fit to, for example, retain the same amount of bone mass displacement. At that point, the surgeon may also determine the size of a bore hole necessary to achieve the optimal displacement, and choose a drill (or other tool) that corresponds to the size of that bore hole.

Still further, the quality of the bone may be determined preoperatively to create a patient-specific guide for later use during the implant procedure. For example, assume again a surgical implant procedure is to be performed with an implant having a fixation feature in the form of a cylindrical peg. As described above, it may be determined from pre-operatively determined bone quality information that, for the particular patient, a greater interference fit is desired between the bore hole in the bone and the fixation feature. Based on this information, a surgical guide for use in the implant procedure may be produced specifically for the particular patient. The guide may include, for example, a guide hole for a drill that is sized to correspond to the bore hole to be made in the bone for the greater interference fit. So, although the implant is not designed specifically for the patient in this case, the guide for use in the surgery is designed specifically for the patient to maintain an ideal engagement characteristic between the implant and the patient.

Figure 4A:
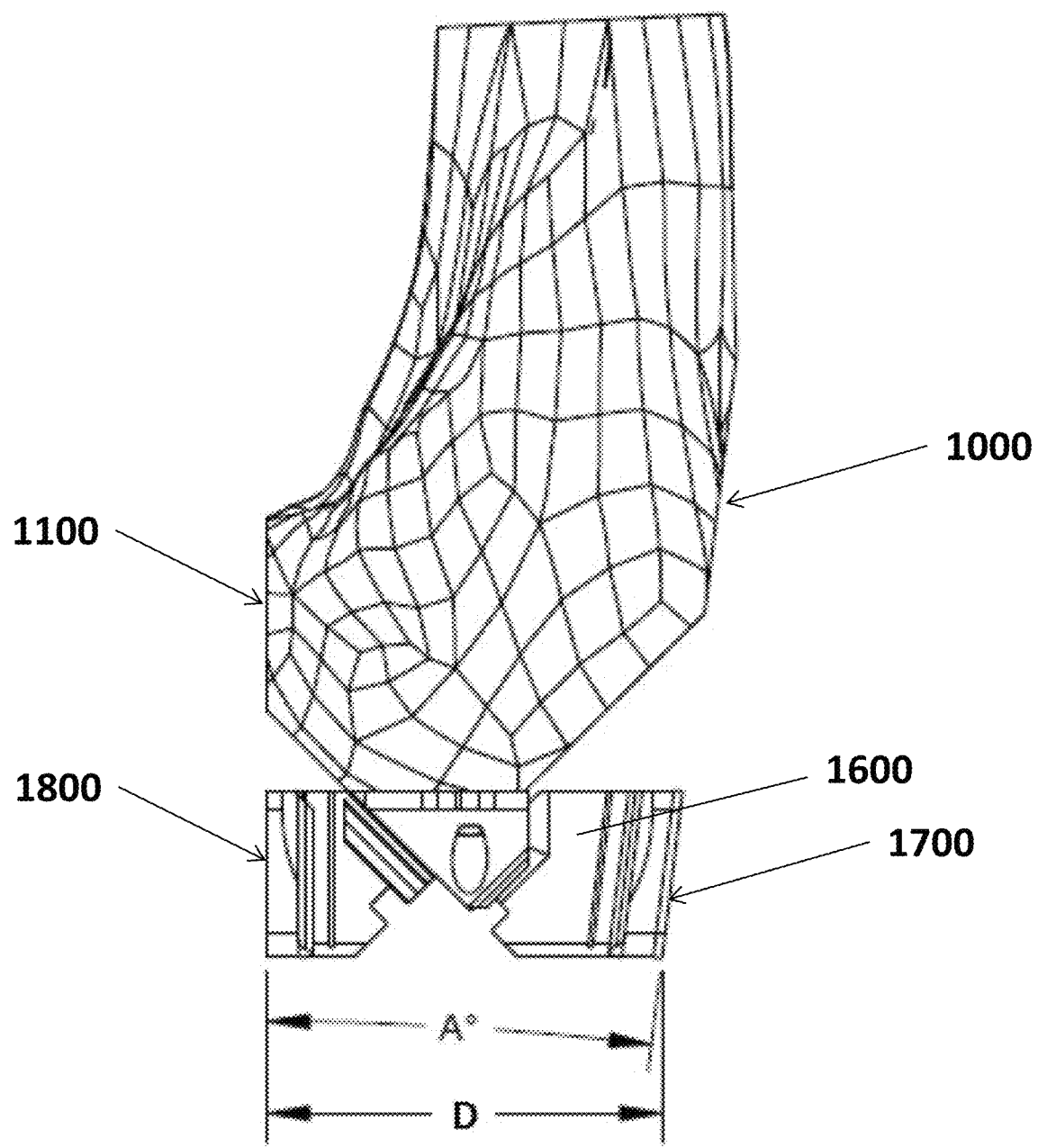
FIG. 4A is a schematic view of a cutting guide adjacent a distal femur.
Figure 4B:
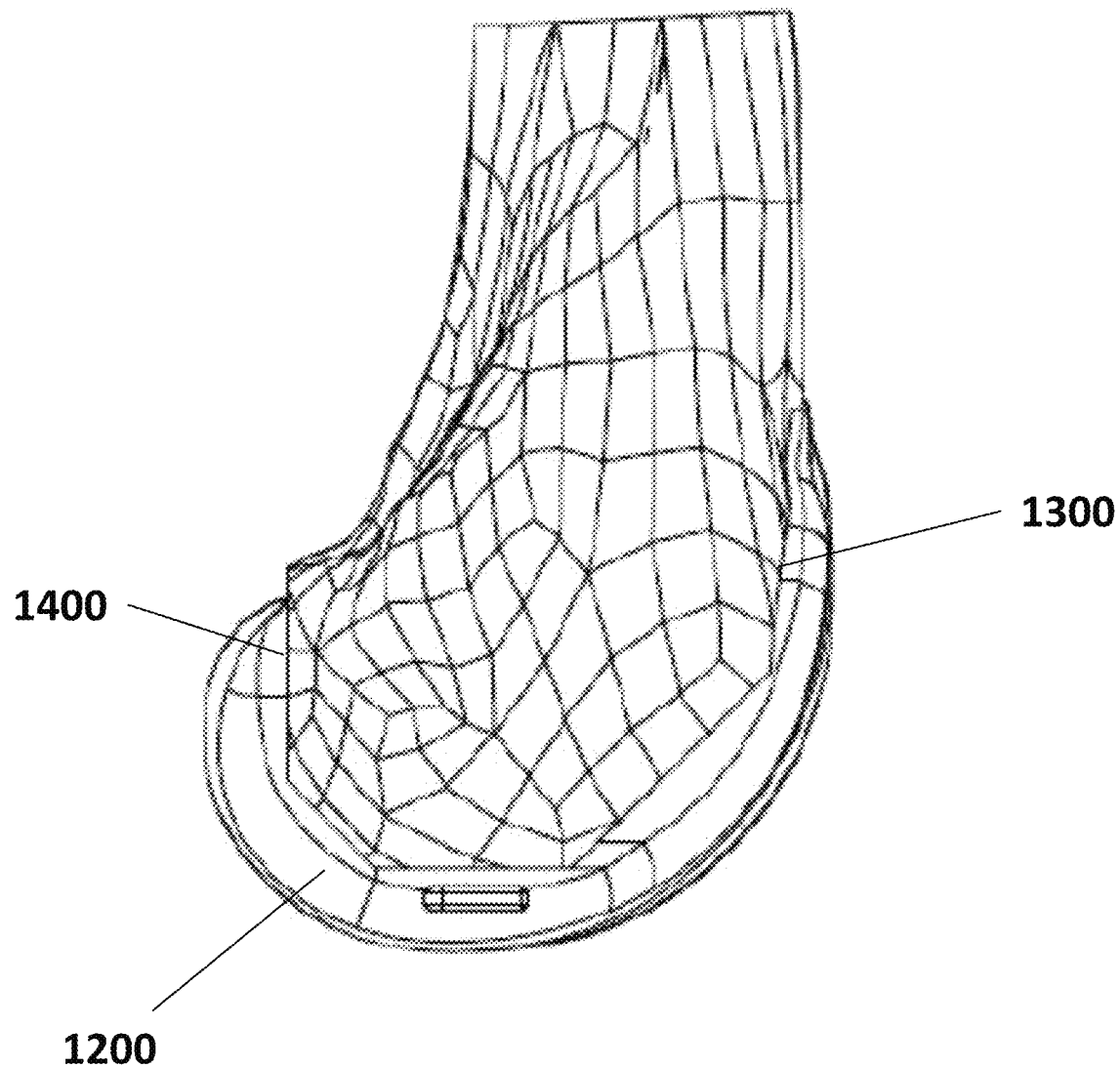
FIG. 4B is a schematic view of a prosthetic femoral component coupled to the cut distal femur of FIG. 5A.

In another example, the patent-specific guide may be for making substantially planar resection cuts in a bone. For example, a number of substantially planar resection cuts may be made to the distal end of a femur in preparation for implantation of a prosthetic femoral component. As shown in FIG. 4A, these may include a substantially planar cut to the anterior femur 1000 and a substantially planar cut to the posterior femur 1100. In this case, the prosthetic femoral component 1200 (FIG. 4B) may have bone-contacting surfaces 1300 and 1400 that generally correspond to the anterior and posterior cuts 1000 and 1100, respectively. The fit between the anterior and posterior surfaces of the femoral component 1300 and 1400 and the anterior and posterior femoral resections 1000 and 1100 may be an interference fit such that opposing surfaces of the femoral component act as a fixation feature. If the cuts are made manually, a patient-specific guide 1600 may be created to provide the desired interference fit based on bone quality data obtained from image data. For example, cutting slots or cutting guide surfaces 1700 and 1800 may be positioned to provide a greater interference fit if the patient has relatively low bone density. So, as shown in FIG. 4A, angle A° and/or distance D between cutting guide surfaces 1700 and 1800 may be increased or decreased to provide the desired interference fit between the distal femur and the femoral component. In other words, parameter being optimized may be the distance between at least two substantially opposing prepared bone surfaces.

Figure 5:
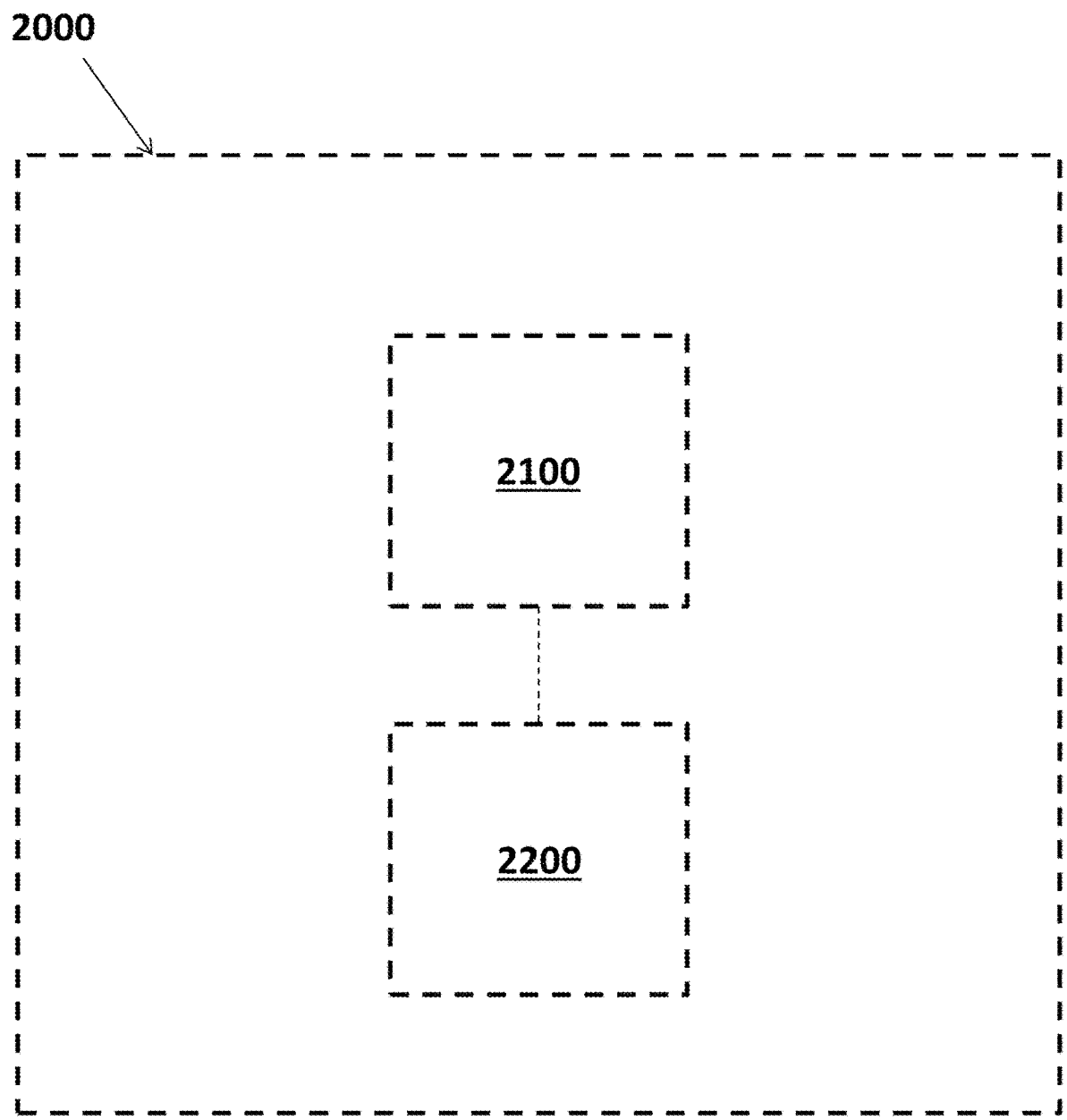
FIG. 5 is a diagrammatic illustration of a system according to the present disclosure.

Even further, the quality of the bone may be determined preoperatively to alter or create a patient-specific robotic tool operation parameter. For example, if an implant with a curved keel is intended to be used in a surgery, information derived from bone quality data may be used to alter or create a particular pathway or trajectory of a robotically controlled resection tool so that a precise resection, in the form of a bore hole following a particular path, is created to mate with the curved keel of the implant. It should be understood that patient-specific robotic paths may apply to other situations not involving an implant with a curved keels. Another patient-specific robotic tool operation parameter that may be altered or created based on information derived from bone quality is a constraint volume or haptic volume specific to the patient. For example, during a procedure using a robotic arm, a particular constraint volume may be used so that the robotic arm has pre-set constraints as to how far the robot arm may move in three-dimensions, helping ensure that the robot arm stays within a desirable range of positions. A similar concept is the haptic volume, refers to the boundary of spatial movement of the robot arm past which tactile feedback is provided to the operator controlling the arm to alarm him to the fact that the robot arm is nearing the edge of the constraint volume. In each case, depending on the patient-specific bone quality information derived from image data, the boundaries of the constraint volume or haptic constraint may be optimized for the particular patient. An overview of systems that may be involved in the disclosure described above is illustrated in FIG. 5. As shown in FIG. 5, system 2000 may include a device 2100 and a computer 2200 operatively connected to device 2100. Device 2100 may be configured to obtain bone quality data corresponding to a bone of a joint. So, for example, device 2100 may be a medical imager, such as a CT scanner or a physical indenter. It should be understood that device 2100 may also include a computer or other processing device operatively connected to the device 2100 to perform desired calculations based on image data obtained by, or stored in, device 2100. Computer 2200 may be adapted to determine the one or more resection parameters based on the bone quality data in order to substantially achieve one or more ideal engagement characteristics between the bone and a fixation feature of the implant. The one or more ideal engagement characteristics may correspond to an optimal press-fit between the fixation feature and the bone, as described in greater detail above. It should be noted that computer 2200 need not be a separate physical device from device 2100, and system 2000 may comprise a single physical object. Alternatively, device 2100 and computer 2200 may each comprise multiple apparatus configured to perform the function of device 2100 and computer 2200, respectively.

Although examples are given herein in the context of a knee implant, the concepts described herein may apply to any implant that engages bones, whether articular implants or not. For example, the concepts described herein may be used to optimize engagement of the femoral stem of a hip implant with a cavity created or resurfaced within a patient's femur. An example of a non-articular implant to which the concepts described herein may apply is a bone plate or a system of bone plates. Generally, bone plates engage the bone via one or more screws extending through the bone plate(s) into the bone. Often, a hole is pre-drilled into the bone prior to threading the screw into the bone. Similar to the fixation features in the form of a peg or multiple pegs, the size of the pre-drilled hole to receive the screw may be increased or decreased based on the bone quality information derived from image data. Further, the bone quality information may suggest that a pre-drilled hole is not desirable, and rather that a self-tapping screw should be used for ideal engagement with the bone. As should be clear, the concepts described herein may also facilitate a user in choosing between one or more of a variety of potential implants to find the implant that will provide the most desired engagement characteristics with the bone. Similarly, applying the concepts described herein may allow a surgeon to determine that a press-fit alone will not provide sufficient engagement characteristics, but rather that bone cement (or other suitable adhesive) should be used alone or in combination with the press-fit.

Figure 6:
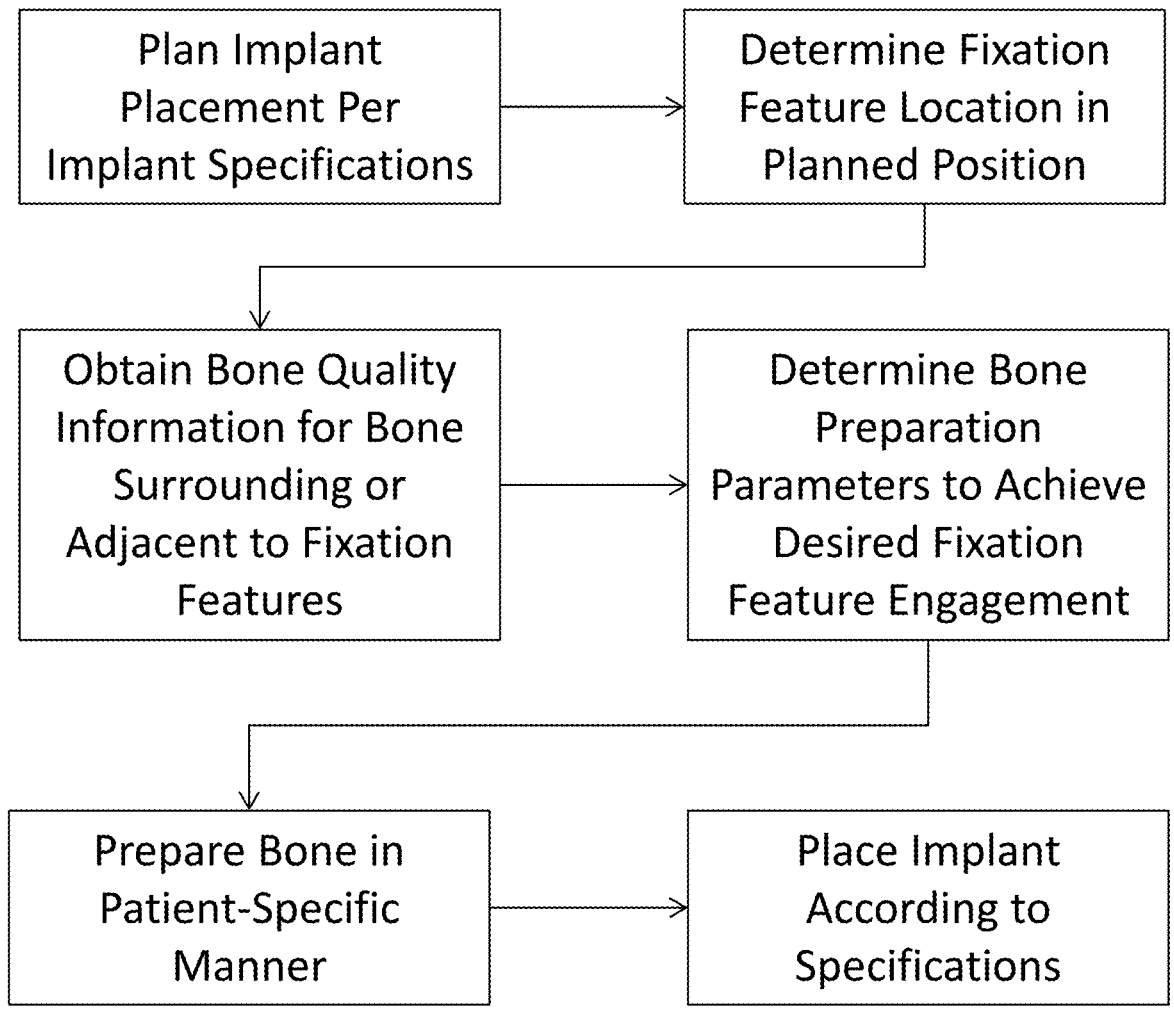
FIG. 6 is a flow chart of a method according to one aspect of the disclosure.
Figure 7:
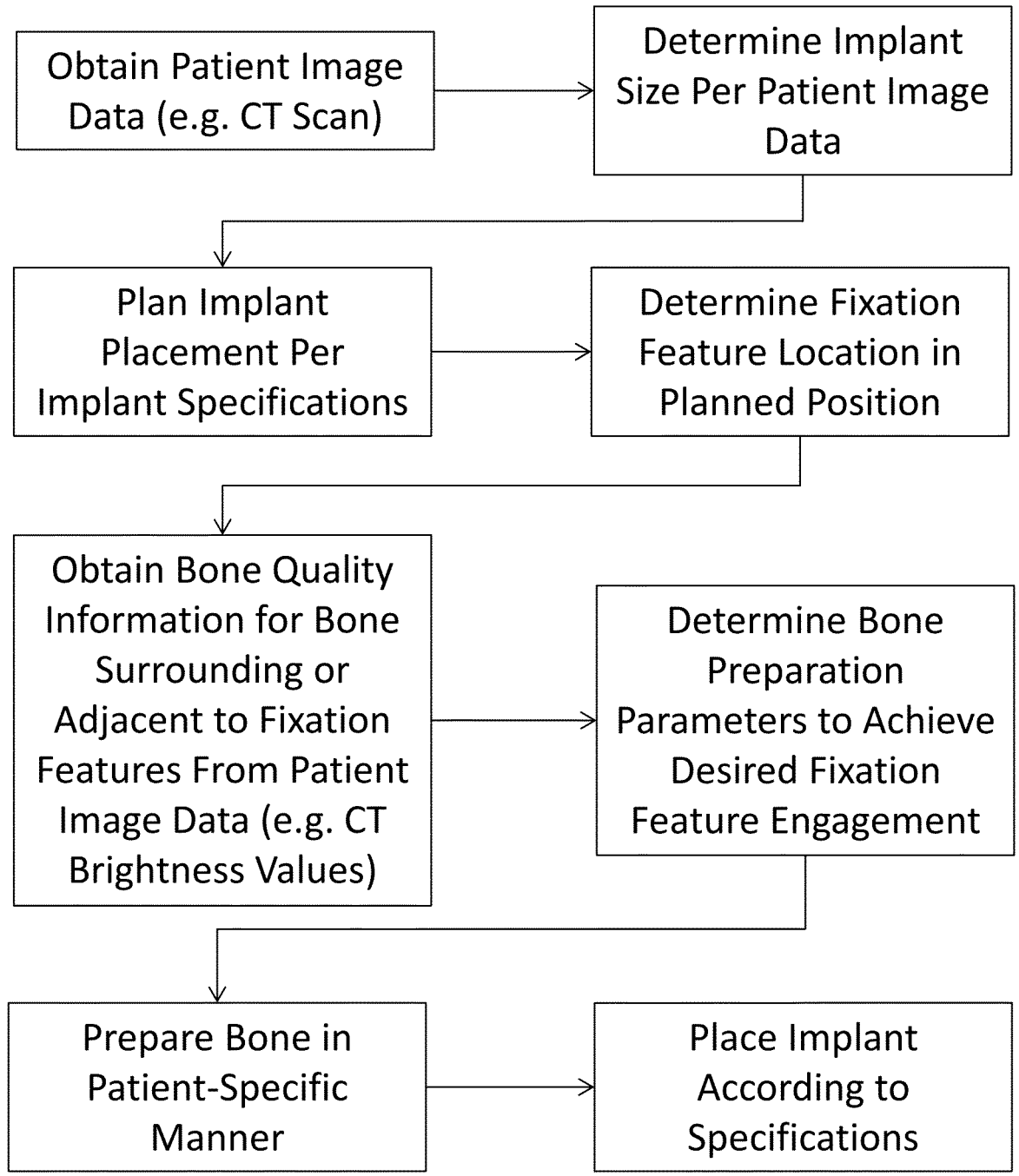
FIG. 7 is a flow chart of a method according to another aspect of the disclosure.
Figure 8:
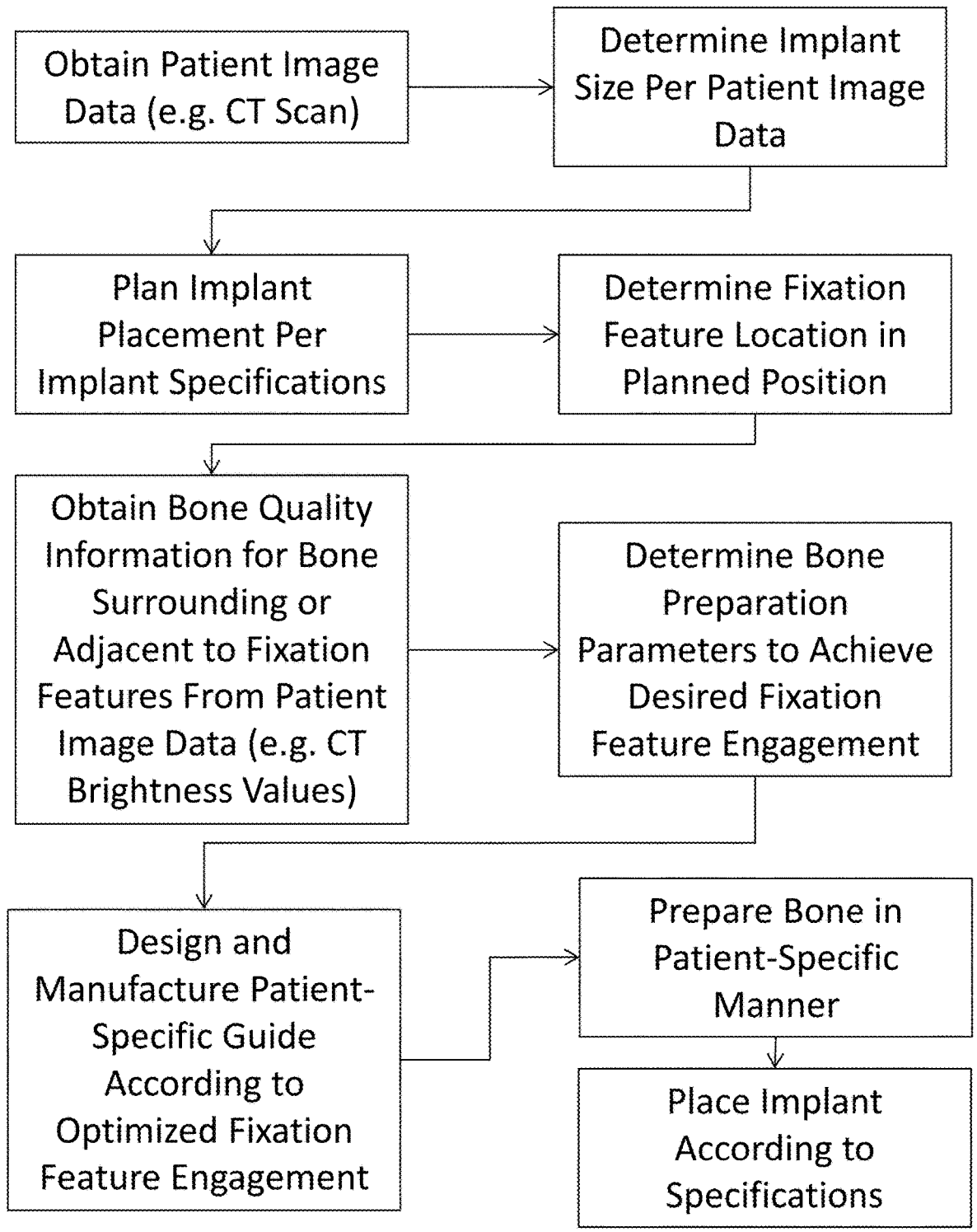
FIG. 8 is a flow chart of a method according to a further aspect of the disclosure.

Flow charts illustrating steps of methods according to certain aspects of the disclosure are shown in FIGS. 6-8. For example, as shown in FIG. 6, one method may include planning implant placement based on implant specifications, determining the locations of one or more fixation features of the implant in the planned position, obtaining bone quality information for bone surrounding or adjacent to the desired position of the fixation features, determining bone preparation parameters for achieving the desired fixation feature engagement, preparing the bone in a patient-specific manner, and placing the implant according to specifications.

As shown in FIG. 7, one method may include obtaining patient image data, for example via a CT scan, determining the implant size based on the patient image data, planning the placement of the implant based on the implant specifications, determining the fixation feature locations in the planned position, obtaining bone quality information for bone surrounding or adjacent to the planned location of the fixation features based on patient image data (e.g. CT brightness values), determining bone preparation parameters to achieve the desired fixation feature engagement, preparing the bone in a patient-specific manner, and placing the implant according to the specifications.

As shown in FIG. 8, another method may include obtaining patient image data, for example via a CT scan, determining the implant size based on the patient image data, planning the placement of the implant based on the implant specifications, determining the fixation feature locations in the planned position, obtaining bone quality information for bone surrounding or adjacent to the planned location of the fixation features based on patient image data (e.g. CT brightness values), determining bone preparation parameters to achieve the desired fixation feature engagement, designing and manufacturing one or more patient-specific guides according to the optimized fixation feature engagement, preparing the bone in a patient-specific manner, and placing the implant according to the specifications.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features or steps described in relation to one aspect of the disclosure may be combined with features or steps described in relation to another aspect of the disclosure. In addition, although methods may be described as having a number of steps, the steps do not need to be completed in the exact order described, unless explicitly noted otherwise or required by the context of the steps.

The invention claimed is:

1. A method of performing surgery on a patient comprising:
providing a prosthetic femoral component having a planar anterior bone-contacting surface and a planar posterior bone-contacting surface, the anterior bone-contacting surface being spaced apart a first distance from the posterior bone-contacting surface;
obtaining bone density data of a distal femur of the patient;
resecting the distal femur of the patient to provide a planar anterior femoral surface and a planar posterior femoral surface, the anterior femoral surface being spaced apart a second distance from the posterior femoral surface, the second distance being smaller than the first distance to provide an interference fit between the prosthetic femoral component and the resected distal femur; and
implanting the prosthetic femoral component onto the resected distal femur,
wherein the anterior bone-contacting surface and the posterior bone-contacting surface correspond to the anterior femoral surface and the posterior femoral surface, respectively, wherein a difference between the first distance and the second distance is based upon the obtained bone density data of the distal femur, wherein the bone density data is derived from image data, wherein resecting the distal femur is performed manually with a manual resection tool and a patient-specific cutting guide, wherein the patient-specific cutting guide includes an anterior cutting guide slot or surface and a posterior cutting guide slot or surface, wherein resecting the distal femur includes passing the manual resection tool through the anterior cutting guide slot or along the anterior cutting guide surface of the patient-specific cutting guide to form the planar anterior femoral surface and through the posterior cutting guide slot or along the posterior cutting guide surface of the patient-specific cutting guide to form the planar posterior femoral surface, wherein a distance between the anterior cutting guide slot or surface and the posterior cutting guide slot or surface may be increased or decreased to provide an optimized interference fit between the prosthetic femoral component and the resected distal femur.

2. The method of claim 1, wherein the image data is CT (computed tomography) image data.

3. The method of claim 2, wherein the step of obtaining bone density data includes calculating one or more Hounsfield values from the CT image data.

4. The method of claim 1, wherein the bone density data is derived from image data of a single individual.

5. The method of claim 1, wherein the bone density data corresponds to a population.

6. The method of claim 1, wherein the bone density data is obtained intraoperatively.

* * * * *